United States Patent
Rains et al.

(10) Patent No.: US 7,946,154 B2
(45) Date of Patent: May 24, 2011

(54) HYDRAULIC FLUID DETERMINATION SYSTEM AND METHOD

(75) Inventors: Mark A. Rains, Indianapolis, IN (US); Randall S. Conn, Indianapolis, IN (US)

(73) Assignee: GM Global Technology Operations LLC, Detroit, MI (US)

( * ) Notice: Subject to any disclaimer, the term of this patent is extended or adjusted under 35 U.S.C. 154(b) by 4 days.

(21) Appl. No.: 12/414,266

(22) Filed: Mar. 30, 2009
(Under 37 CFR 1.47)

(65) Prior Publication Data
US 2009/0277253 A1    Nov. 12, 2009

Related U.S. Application Data

(60) Provisional application No. 61/051,799, filed on May 9, 2008.

(51) Int. Cl.
*G01N 33/26*        (2006.01)

(52) U.S. Cl. ...................................................... 73/53.05

(58) Field of Classification Search .................. 73/53.05
See application file for complete search history.

(56) References Cited

U.S. PATENT DOCUMENTS

| | | | | |
|---|---|---|---|---|
| 2003/0188570 | A1* | 10/2003 | Kasen et al. | 73/61.46 |
| 2009/0241645 | A1* | 10/2009 | Rains et al. | 73/53.05 |

* cited by examiner

*Primary Examiner* — Hezron Williams
*Assistant Examiner* — Nathaniel Kolb

(57) ABSTRACT

A system for determining the type of hydraulic fluid employed in a transmission includes a translating valve, a valve position sensor, a hydraulic fluid temperature sensor, and a controller. The valve position sensor is operable to measure the actual time the valve takes to translate within the hydraulic fluid. The controller is operable to compare the actual time of valve translation to an expected time of valve translation. If the actual time of valve translation is different than the expected time of valve translation to a predetermined degree, the controller is operable to signal an operator of the motor vehicle or a service technician that the hydraulic fluid being used in the transmission is not meeting operating expectations.

10 Claims, 2 Drawing Sheets

HYDRAULIC FLUID DETERMINATION SYSTEM AND METHOD

CROSS-REFERENCE TO RELATED APPLICATIONS

Figure 1:
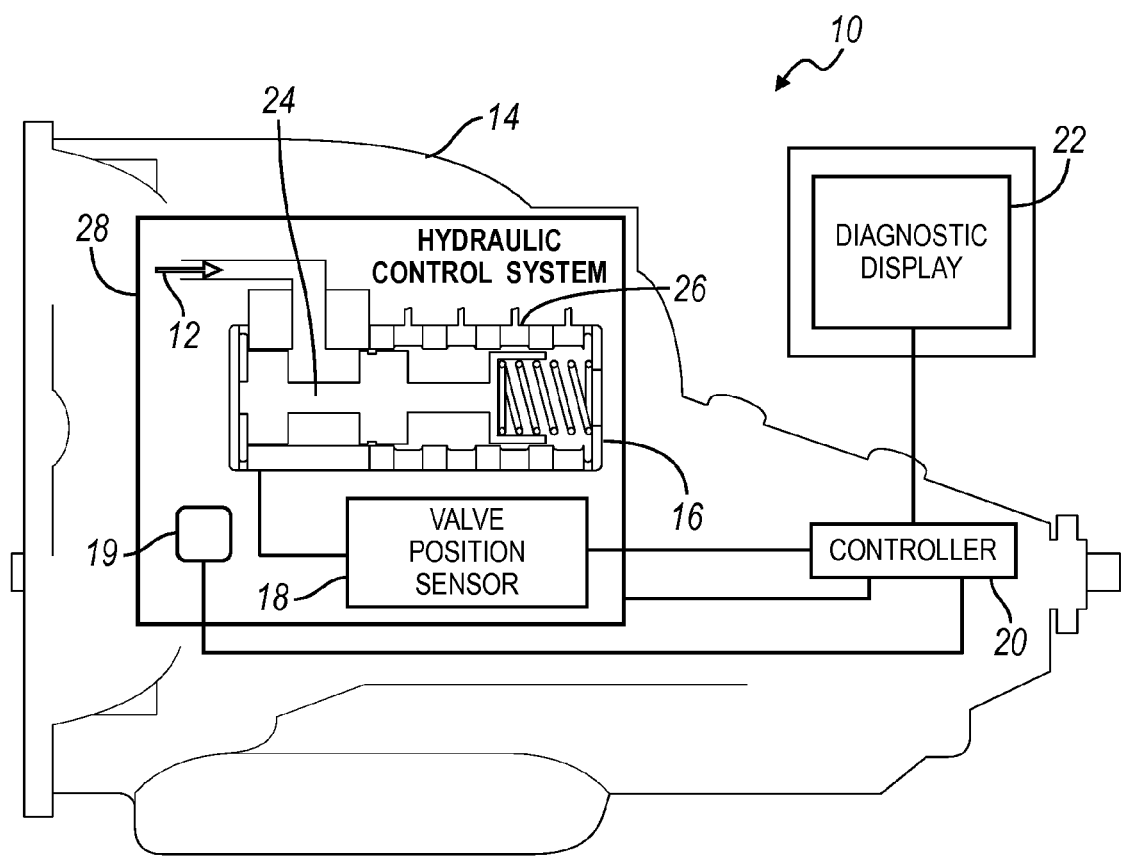

This application claims the benefit of U.S. Provisional Application No. 61/051,799, filed on May 9, 2008. The disclosure of the above application is incorporated herein by reference.

FIELD

The invention relates generally to a hydraulic fluid determination system and method for a motor vehicle, and more particularly to a hydraulic fluid determination system and method having a translatable valve and a controller operable to determine the type of hydraulic fluid in a transmission.

BACKGROUND

The statements in this section merely provide background information related to the present disclosure and may or may not constitute prior art.

A typical automatic transmission employs a hydraulic fluid, such as an oil, to provide lubrication to various transmission components, to provide cooling, and to actuate valves, solenoids, and/or pistons within a hydraulic control system. Various types of hydraulic fluids or oils have specific properties tailored to their intended use. For example, engine oils are intended to be employed in an engine of a motor vehicle while transmission oils are intended to be employed in the transmission of the motor vehicle. These transmission oils are compatible with the components of the transmission and allow the transmission to operate as intended.

However, it is possible that a hydraulic fluid not specified by the transmission may be employed by an operator of the motor vehicle or a service technician. If a hydraulic fluid that is not intended to be used by the transmission is employed, the transmission components may wear more quickly, shift quality can degrade, and the hydraulic fluid life can degrade more quickly than expected. Accordingly, there is room in the art for a system integrated in the motor vehicle that determines if a hydraulic fluid is being employed by the transmission that is not compatible with the transmission.

SUMMARY

The present invention provides a system for determining the type of hydraulic fluid employed in a transmission. The system includes a translating valve, a valve position sensor, a hydraulic fluid temperature sensor, and a controller. The valve position sensor is operable to measure the actual time the valve takes to translate within the hydraulic fluid. The controller is operable to compare the actual time of valve translation to an expected time of valve translation. If the actual time of valve translation is different than the expected time of valve translation to a predetermined degree, the controller is operable to signal an operator of the motor vehicle or a service technician that the hydraulic fluid being used in the transmission is not meeting operating expectations.

Further objects, aspects and advantages of the present invention will become apparent by reference to the following description and appended drawings wherein like reference numbers refer to the same component, element or feature.

DRAWINGS

The drawings described herein are for illustration purposes only and are not intended to limit the scope of the present disclosure in any way.

Figure 2:
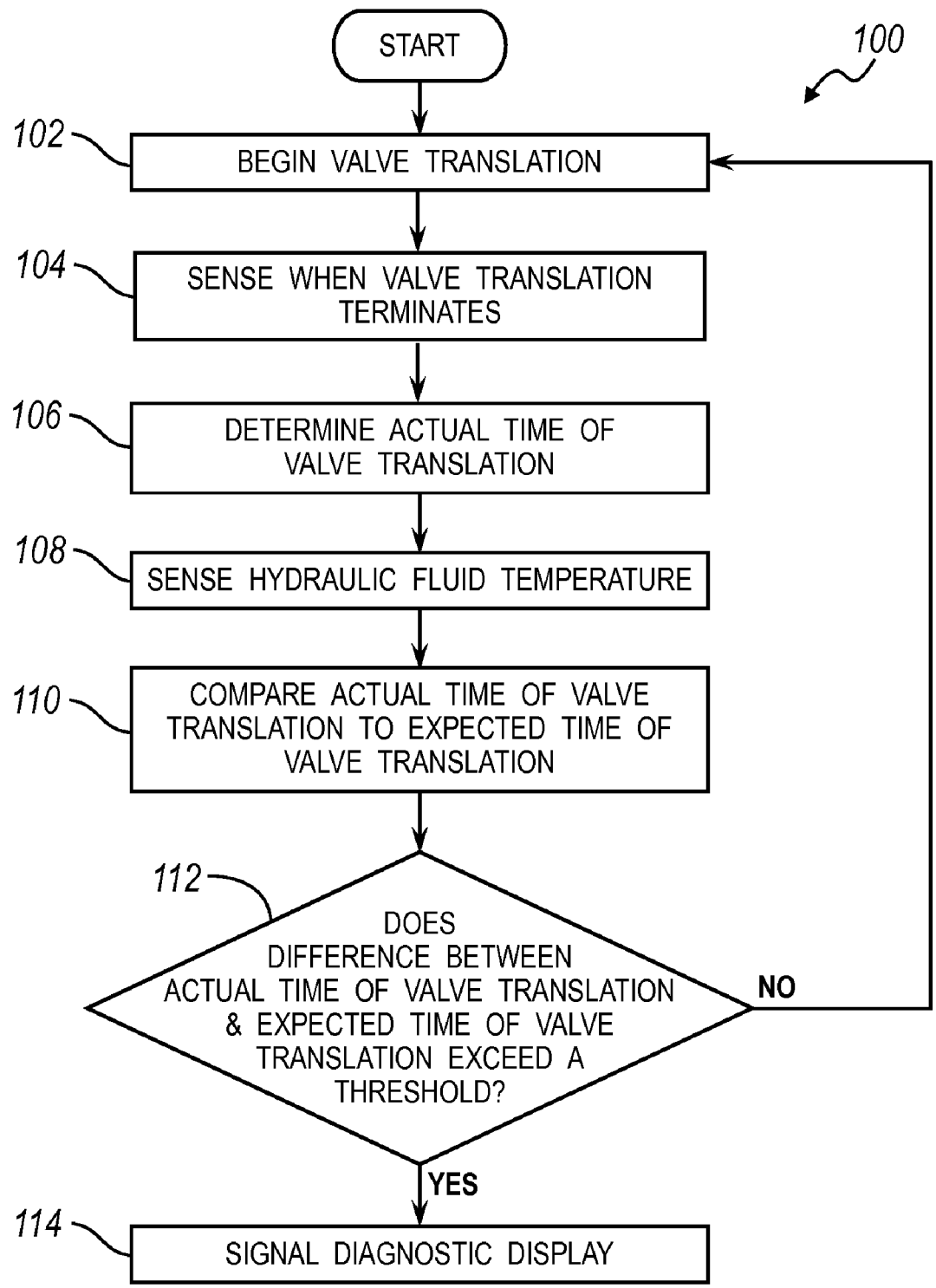

FIG. 1 is a schematic diagram of an embodiment of a hydraulic fluid determination system according to the principles of the present invention; and FIG. 2 is a flow chart of an embodiment of a method of determining the type of a hydraulic fluid using the hydraulic determination system of the present invention.

DETAILED DESCRIPTION

The following description is merely exemplary in nature and is not intended to limit the present disclosure, application, or uses.

With reference to FIG. 1, a hydraulic fluid determination system for use in a motor vehicle is generally indicated by reference number 10. The hydraulic fluid determination system 10 is operable to determine a type of a hydraulic fluid 12 employed in an exemplary transmission 14, as will be described in further detail below. The transmission 14 may have various configurations without departing from the scope of the present invention. The hydraulic fluid determination system 10 includes a valve assembly 16, a valve position sensor 18, a temperature sensor 19, a controller 20, and a diagnostic display 22.

The valve assembly 16 generally includes a valve 24 disposed within a valve body 26. The valve 24 is translatable or slidable within the valve body 26 between at least two positions. The valve 24 is in fluid communication with the hydraulic fluid 12. In the present embodiment, the valve assembly 16 is part of a hydraulic control system 28 within the transmission 14, however, it should be appreciated that the valve assembly 16 may be located within various other subsystems of the transmission 14 without departing from the scope of the present invention. Moreover, the configuration of the valve assembly 16 may vary without departing from the scope of the present invention so long as the valve assembly 16 includes a component in fluid communication with the hydraulic fluid 12 that is moveable between at least two positions.

The valve position sensor 18 is in communication with the valve assembly 16 and is operable to determine the position of the valve 24 within the valve assembly 16. The valve position sensor 18 is preferably a pressure switch located within the hydraulic control system 28 that selectively receives a pressurized hydraulic fluid flow when the valve 24 is in at least one of the two positions. Accordingly, receipt of the pressurized hydraulic fluid flow by the valve position sensor 18 is indicative of the position of the valve 24. However, it should be appreciated that the valve position sensor 18 may take various other forms without departing from the scope of the present invention. For example, the valve position sensor 18 may be an electromechanical switch or other kind of sensor.

The temperature sensor 19 is in communication with the hydraulic fluid 12 and is operable to sense the temperature of the hydraulic fluid 12 within the transmission 14. The temperature sensor 19 may take various forms without departing from the scope of the present invention.

The controller 20 is, for example, a transmission controller, a vehicle control module, or other electronic device having a preprogrammed digital computer or processor, control logic, memory used to store data, and at least one I/O peripheral. However, other types of controllers may be employed without departing from the scope of the present invention. The controller 20 is in communication with the hydraulic control system 28 of the transmission 14, with the valve position sensor 18, and with the temperature sensor 19. More specifically, the controller 20 is configured to receive data signals from the valve position sensor 18 indicative of the position of the valve 24, to receive data signals from the temperature sensor 19 indicative of the temperature of the hydraulic fluid 12, and to send control signals to the hydraulic control system 28.

The diagnostic display 22 is in communication with the controller 20. The diagnostic display 22 is operable to communicate the type of hydraulic fluid 12 within the transmission 14 to an operator or service technician of the motor vehicle. For example, the diagnostic display 22 may be a warning light or digital message displayed on the instrument panel of the motor vehicle or a diagnostic device connected to the controller 20 during maintenance. Moreover, the diagnostic display 22 can be configured to indicate that a more frequent transmission hydraulic fluid change is needed if the hydraulic fluid 12 is determined to be a type not intended for the transmission 14.

Turning now to FIG. 2 and with continued reference to FIG. 1, a method of determining the type of the hydraulic fluid 12 using the hydraulic fluid determination system 10 is generally indicated by reference number 100. The method 100 begins when the valve 24 is translated or moved at step 102. The valve 24 may be translated during normal operation of the transmission 14 or by a specific command from the controller 20 to the hydraulic control system 28.

At step 104 the valve position sensor 18 senses when the valve 24 has completed the translation from the first position to the second position. A data signal indicative of completion of the translation of the valve 24 is communicated to the controller 20. At step 106, the controller 20 determines an actual time of valve translation by comparing the time when the valve 24 began to translate at step 102 to the time the valve 24 finished translating as indicated by the valve position sensor 18. The actual time of valve translation is dependent on what type of hydraulic fluid is in communication with the valve 24 and the temperature of the hydraulic fluid. More specifically, for a given temperature, a hydraulic fluid with high viscosity will cause the valve 24 to move more slowly than a hydraulic fluid with low viscosity. At step 108 the temperature sensor 19 senses the temperature of the hydraulic fluid 12. A data signal indicative of the temperature of the hydraulic fluid 12 is communicated to the controller 20.

At step 110 the controller 20 compares the actual valve translation time determined at step 106 to an expected valve translation time to determine a time difference value. The expected valve translation time is the amount of time the valve 24 is expected to take to translate from the first position to the second position when a type of hydraulic fluid that is compatible with the transmission 14 having a temperature equal to the sensed temperature of the hydraulic fluid 12 is employed. The time difference value is the time difference between the actual valve translation time and the expected valve translation time.

At step 112 the controller 20 compares the time difference value determined at step 110 to a threshold value. The threshold value is a predetermined value set at a limit where it is desirable to indicate to the operator of the motor vehicle or a service technician that the hydraulic fluid 12 is not compatible with the transmission 14. Moreover, various thresholds may be employed, each indicative of a type of hydraulic fluid, such that exceeding a certain threshold or falling within a range of thresholds indicates a certain type of hydraulic fluid within the transmission.

If the time difference value exceeds the threshold value, the method 100 proceeds to step 114 and the controller 20 communicates to the diagnostic display 22 that there is an issue with the hydraulic fluid 12 within the transmission 14. As noted above, this may include reducing the time between scheduled oil changes or indicating that the hydraulic fluid 12 should be changed as soon as possible. Additionally, this information may be stored in the controller until the information is requested during a maintenance check. If the time difference value does not exceed the threshold value, the method 100 returns to step 102 and repeats, thereby providing a real-time and updated check of the status of the hydraulic fluid 12.

The description of the invention is merely exemplary in nature and variations that do not depart from the gist of the invention are intended to be within the scope of the invention. Such variations are not to be regarded as a departure from the spirit and scope of the invention.

We claim the following:

1. A system for determining a type of hydraulic fluid in a transmission, the system comprising:
   a valve assembly having a valve moveable between a first position and a second position;
   a valve position sensor proximate the valve for determining a location of the valve;
   a hydraulic fluid temperature sensor in communication with the hydraulic fluid for determining a temperature of the hydraulic fluid; and
   a controller in communication with the valve position sensor and the hydraulic fluid temperature sensor, the controller having control logic including a first control logic for determining an amount of time that elapses when the valve moves from the first position to the second position, a second control logic for sensing a temperature of the hydraulic fluid, a third control logic for comparing the elapsed time to a predefined time value to determine a time difference value, a fourth control logic for comparing the time difference value to a threshold, and a fifth control logic for initiating a signal indicative of a type of the hydraulic fluid if the time difference value exceeds the threshold.

2. The system of claim 1 wherein the elapsed time is dependent on the temperature of the hydraulic fluid sensed by the hydraulic fluid temperature sensor.

3. The system of claim 2 wherein the predefined time value is a predetermined time interval for the valve to move between the first position and the second position in hydraulic fluid of a predetermined type.

4. The system of claim 1 further comprising a diagnostic display, wherein the signal indicative of the type of the hydraulic fluid is communicated to the diagnostic display.

5. The system of claim 1 wherein the fourth control logic further comprises comparing the time difference value to a plurality of thresholds, wherein each of the plurality of thresholds corresponds to a predetermined type of hydraulic fluid.

6. A method for determining a type of hydraulic fluid in a transmission, the method comprising the steps of:
   determining an amount of time that elapses as a valve moves within the hydraulic fluid between a first position and a second position;
   sensing a temperature of the hydraulic fluid;
   comparing the elapsed time to a predetermined time value to determine a time difference value;
   comparing the time difference value to a threshold; and communicating a signal indicative of a type of the hydraulic fluid if the time difference value exceeds the threshold.

7. The method of claim 6 wherein the elapsed time is dependent on the temperature of the hydraulic fluid sensed by the hydraulic fluid temperature sensor.

8. The method of claim 7 wherein the predefined time value is a predetermined time interval for the valve to move between the first position and the second position in hydraulic fluid of a predetermined type.

9. The method of claim 6 wherein the signal indicative of the type of the hydraulic fluid is communicated to a diagnostic display.

10. The method of claim 6 wherein the step of comparing the time difference value to a threshold further comprises comparing the time difference value to a plurality of thresholds, wherein each of the plurality of thresholds corresponds to a predetermined type of hydraulic fluid.

* * * * *